(12) United States Patent
Zhang et al.

(10) Patent No.: US 9,321,779 B2
(45) Date of Patent: Apr. 26, 2016

(54) INTERMEDIATE FOR SYNTHESIZING CASPOFUNGIN AND PREPARATION METHOD THEREOF

(75) Inventors: Fuyao Zhang, Shanghai (CN);
Xiaoming Shen, Shanghai (CN);
Gaoqiang Hu, Shanghai (CN);
Piaoyang Sun, Lianyungang (CN)

(73) Assignee: UniTris Biopharma Co., Ltd., Pudong, Shanghai (CN)

( * ) Notice: Subject to any disclaimer, the term of this patent is extended or adjusted under 35 U.S.C. 154(b) by 7 days.

(21) Appl. No.: 14/113,512

(22) PCT Filed: Mar. 21, 2012

(86) PCT No.: PCT/CN2012/072714
§ 371 (c)(1),
(2), (4) Date: Oct. 23, 2013

(87) PCT Pub. No.: WO2012/146099
PCT Pub. Date: Nov. 1, 2012

(65) Prior Publication Data
US 2014/0058082 A1    Feb. 27, 2014

(30) Foreign Application Priority Data

Apr. 28, 2011 (CN) .......................... 2011 1 0107633

(51) Int. Cl.
*C07D 487/14* (2006.01)
*C07K 7/56* (2006.01)

(52) U.S. Cl.
CPC ............. *C07D 487/14* (2013.01); *C07K 7/56* (2013.01)

(58) Field of Classification Search
None
See application file for complete search history.

(56) References Cited

U.S. PATENT DOCUMENTS

| | | | |
|---|---|---|---|
| 5,552,521 A | 9/1996 | Belyk et al. | |
| 5,936,062 A | 8/1999 | Leonard et al. | |
| 2010/0168415 A1 | 7/2010 | Lee et al. | |
| 2012/0190815 A1* | 7/2012 | Xu et al. ....................... | 530/317 |

FOREIGN PATENT DOCUMENTS

| | | |
|---|---|---|
| CN | 101648994 A | 2/2010 |
| CN | 101792486 A | 8/2010 |
| WO | 02/083713 A2 | 10/2002 |
| WO | 2007/057141 A1 | 5/2007 |
| WO | WO2011/014990 * | 2/2011 |
| WO | 2012077853 A1 | 6/2012 |
| WO | WO2012/093293 * | 6/2012 |

OTHER PUBLICATIONS

Int'l Search Report issued on Jun. 14, 2012 in Int'l Application No. PCT/CN2012/072714.
Leng et al, "The Clinical Application of Caspofungin and Its Research Progress of Chemical Synthesis," Hebei Huagong, vol. 34, No. 1, pp. 19-22 (Jan. 2011).

* cited by examiner

*Primary Examiner* — James H Alstrum Acevedo
*Assistant Examiner* — Tara Martinez
(74) *Attorney, Agent, or Firm* — Panitch Schwarze Belisario & Nadel LLP

(57) ABSTRACT

The present invention relates to an intermediate, as represented by formula (I), for synthesizing caspofungin, and a preparation method thereof. The intermediate enables efficient preparation of caspofungin.

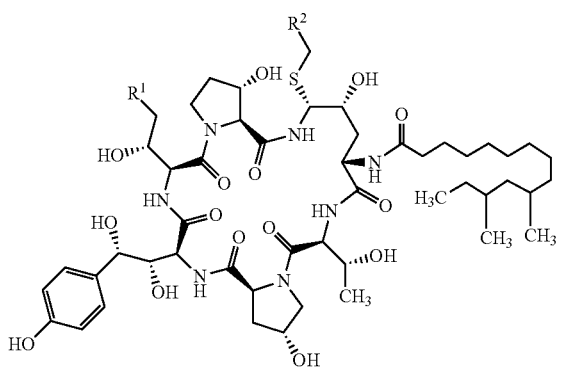

(I)

21 Claims, No Drawings

INTERMEDIATE FOR SYNTHESIZING CASPOFUNGIN AND PREPARATION METHOD THEREOF

CROSS-REFERENCE TO RELATED APPLICATIONS

This application is a Section 371 of International Application No. PCT/CN2012/072714, filed on Mar 21, 2012, which was published in the Chinese language on Nov 1, 2012, under International Publication No. WO 2012/146099 A1, and the disclosure of which is incorporated herein by reference.

FIELD OF INVENTION

The invention relates to an intermediate for the synthesis of caspofungin and a preparation method thereof.

BACKGROUND FOR THE INVENTION

Caspofungin is a new member of echinocandin antifungal drugs, which was developed in the early 21$^{st}$ century and first marketed in the United States in February 2001. It has a novel acting mechanism, which kills the fungus by inhibiting the enzyme β-D-glucan synthase, thus disturbing the integrity of the fungal cell wall. Caspofungin has the advantages of broad antifungal activities, no cross resistance and low toxicity, and it can be used to treat systemic fungal infections, including various invasive candidiasis and aspergillosis. It is more effective than amphotericin B, especially toward common refractory candidiasis.

Caspofungin has been semi-synthesized from the biologically fermented intermediate pneumocandin B0 (PB0). Various synthetic methods for caspofungin have been extensively described in patents such as U.S. Pat. No. 5,552,521, U.S. Pat. No. 5,936,062, US20100168415, WO2002083713, WO2007057141, CN101648994, CN101792486, etc. All these methods involve the key intermediate of formula I' with the thiol substituted aromatic compound (HS—Ar), e.g. thiophenol, as a leaving group.

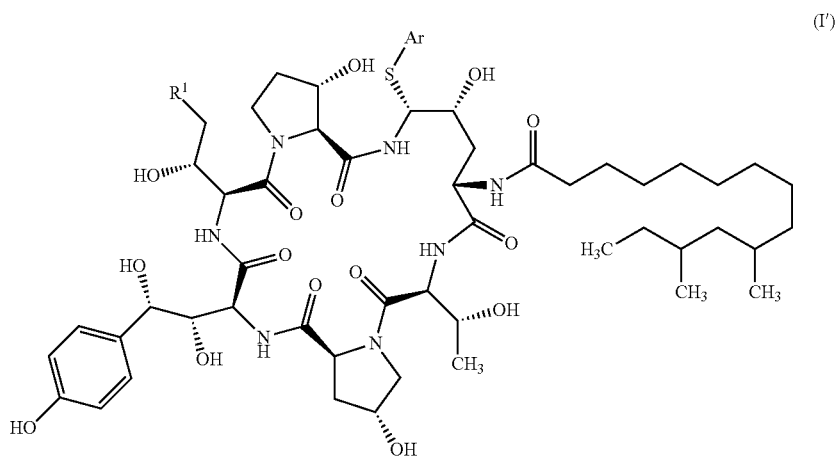

(I')

Due to the regioselectivity in the replacement of thiol substituted aromatic compounds, multiple chromatography purifications were required to afford the pure intermediates and final product in the preparation of caspofungin, which led to low yield, high cost, complex operation, and the like. Thus, there is still a need to develop new preparation methods for caspofungin.

DETAILED DESCRIPTION OF THE INVENTION

This invention relates to an intermediate for the synthesis of caspofungin and a preparation method thereof. The synthesis process of caspofungin can be simplified, thus increasing its synthetic efficiency by the said intermediate.

An object of the present invention is to provide an intermediate of formula (I) for the synthesis of caspofungin,

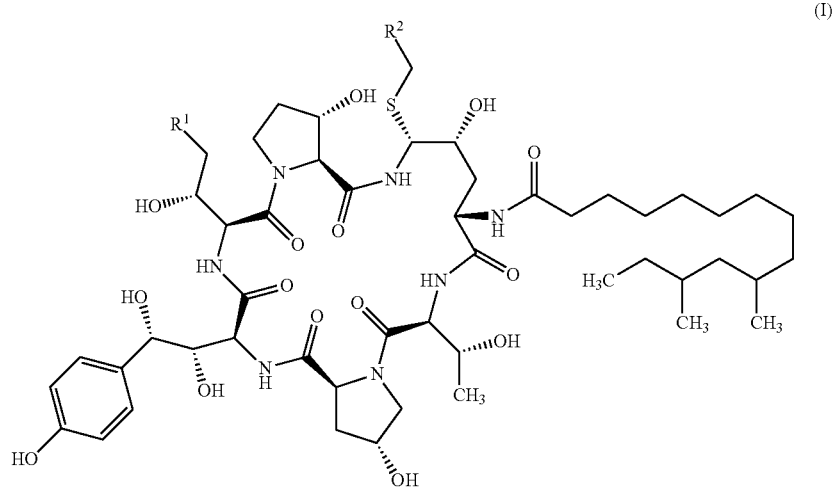

(I)

wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or amino protecting group, such as Boc or Cbz; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle, preferably a five- or six-membered ring; and $R^6$ and $R^7$ are not amino or methoxy at the same time.

Preferably, $R^1$ is $C(=O)NH_2$, CN or $CH_2NH_2$; $R^2$ is CN, $CO_2H$, $CO_2Me$, $CO_2Et$, $CO_2Bu$, $CO_2{}^tBu$, $CO_2Ph$, $C(=O)NH_2$, $C(=O)NMe_2$, $C(=O)NHEt$, $C(=O)NHBu$, $C(=O)NHCH_2CH_2NH_2$, $C(=O)NH^cPr$, $C(=O)NH^iPr$, $C(=O)NH^cPen$, $C(=O)NHBu$, $C(=O)NHPh$ or phenyl, more preferably $R^2$ is $CO_2H$, $CO_2Me$, or $C(=O)NHCH_2CH_2NH_2$.

In a preferred embodiment of the present invention, in formula (I), $R^1$ is $CH_2NH_2$; $R^2$ is $CO_2Me$.

Another object of the present invention is to provide a preparation method of the intermediate of formula I, which involves the reaction of an intermediate of formula (II) with a thiol compound of formula (III) in the presence of organic boronic acid and organic sulfonic acid to afford intermediate I of formula (I);

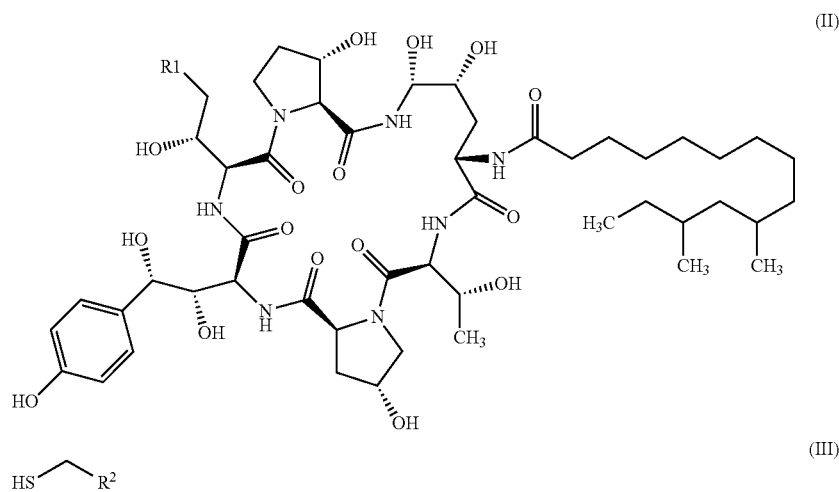

(II)

(III)

wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or amino protecting group, such as Boc or Cbz; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle, preferably a five- or six-membered ring; and $R^6$ and $R^7$ are not amino or methoxy at the same time.

The present invention also provides a preparation method of caspofungin including the following steps:

1) Reaction of an intermediate of formula (II) with a thiol compound of formula (III) in the presence of organic boronic acid and organic sulfonic acid affords intermediate I of formula (I);

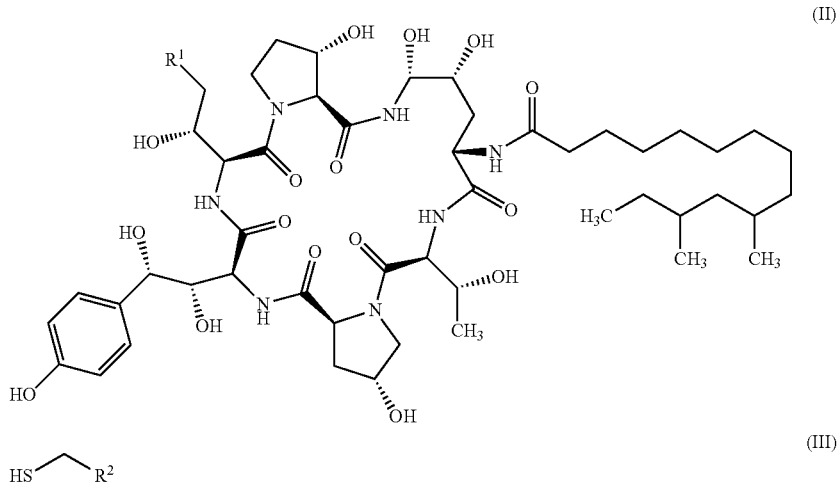

(II)

(III)

wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or amino protecting group, such as Boc or Cbz; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle, preferably a five- or six-membered ring; and $R^6$ and $R^7$ are not amino or methoxy at the same time;

2) Reaction of an intermediate of formula (I) with ethylenediamine affords caspofungin finally, in which $R^1$ is reduced to $CH_2NH_2$ or undergoes amino-deprotection before or after reaction with ethylenediamine when $R^1$ is not $CH_2NH_2$, (I)

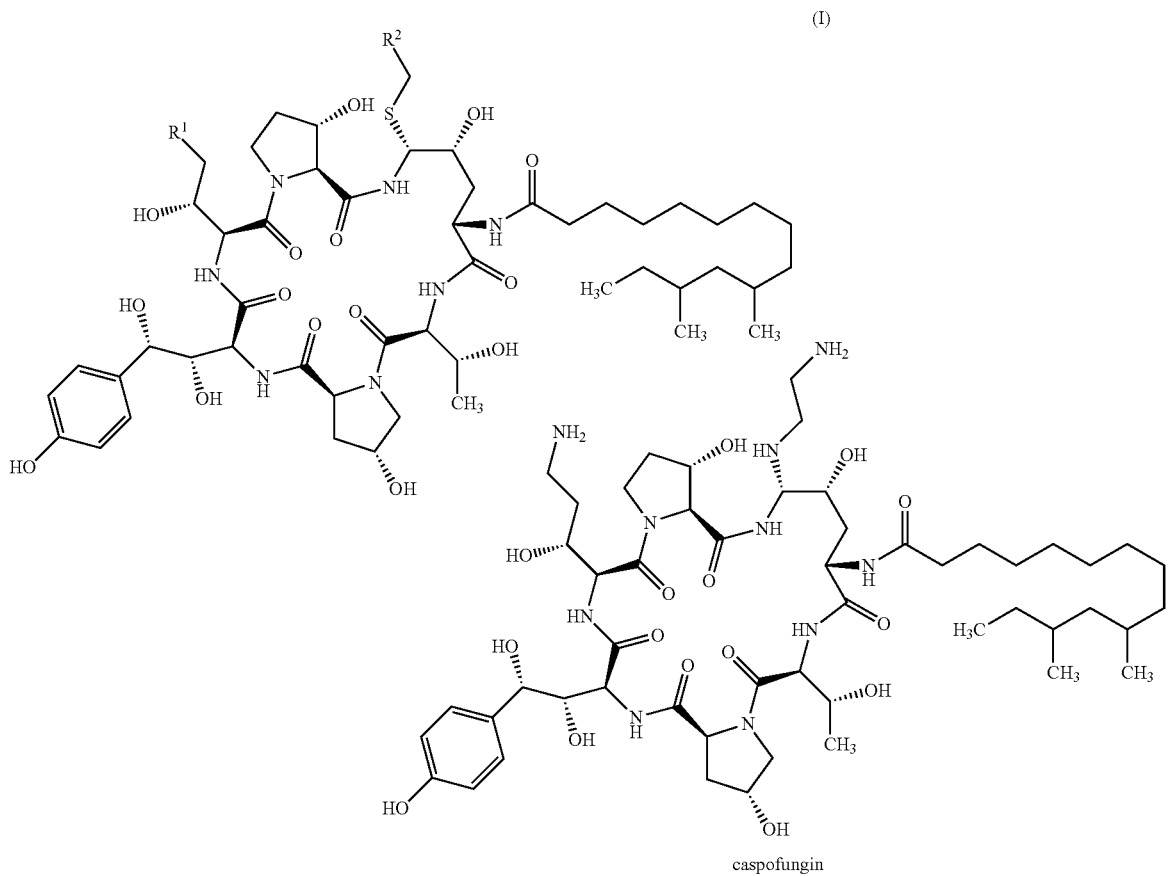

caspofungin wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or amino protecting group, which preferably is Boc or Cbz; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle, preferably a five- or six-membered ring; and $R^6$ and $R^7$ are not amino or methoxy at the same time.

In a preferred embodiment of the present invention, said method comprises the following steps:
1) Reaction of intermediate IIA of formula (IIA) with thiol compound III of formula (III) in the presence of organic boronic acid and organic sulfonic acid affords intermediate IA of formula (IA),
2) Reaction of intermediate IA of formula (IA) with ethylenediamine affords caspofungin.

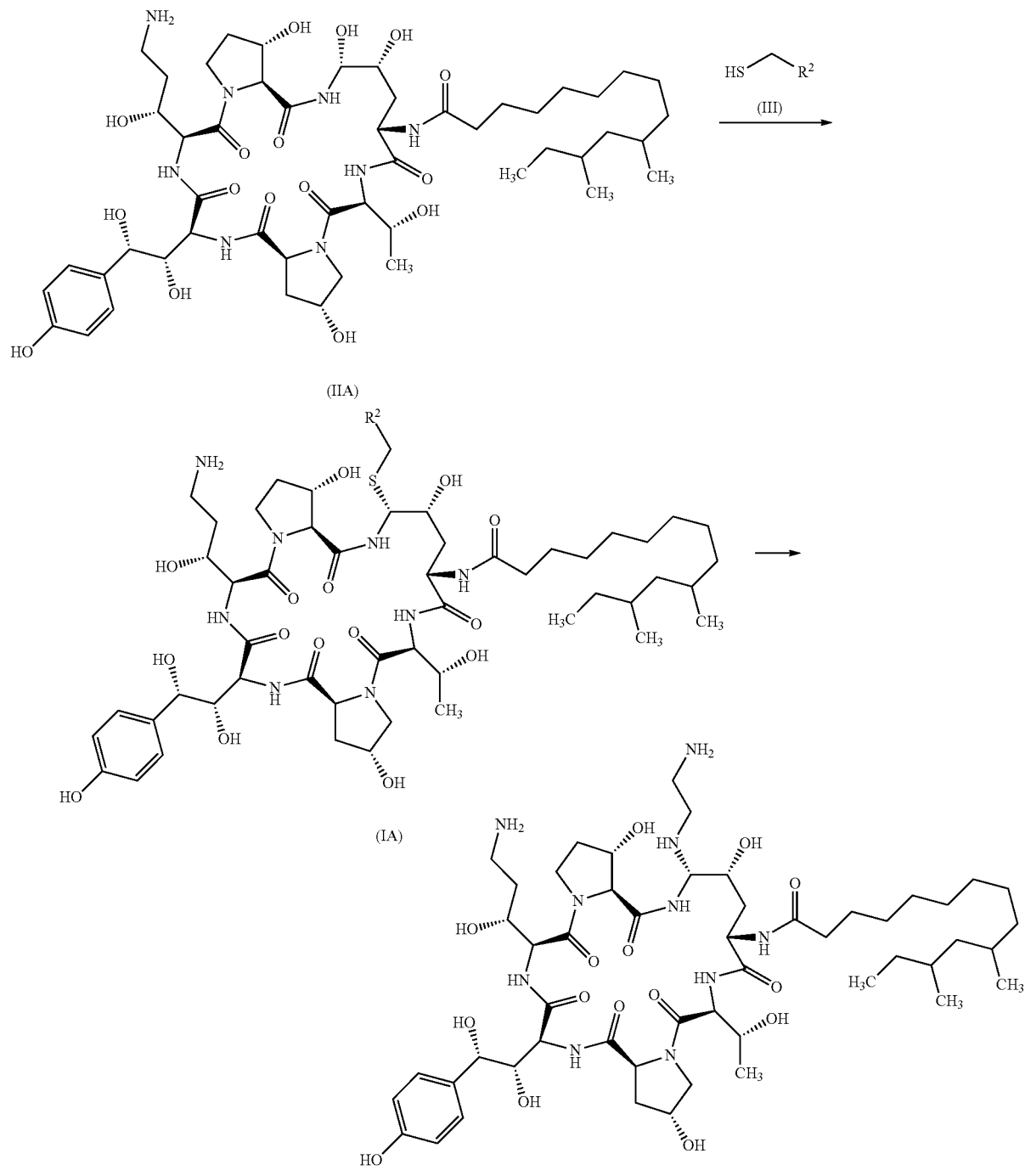

caspofungin

In another preferred embodiment of the present invention, said method comprises the following steps:

1) Reaction of intermediate IIB of formula (IIB) with thiol compound III of formula (III) in the presence of organic boronic acid and organic sulfonic acid affords intermediate IB of formula (IB),
2) Reaction of intermediate IB of formula (IB) with ethylenediamine affords intermediate IVB of formula (IVB), and
3) Intermediate of formula (IVB) is reduced to caspofungin.

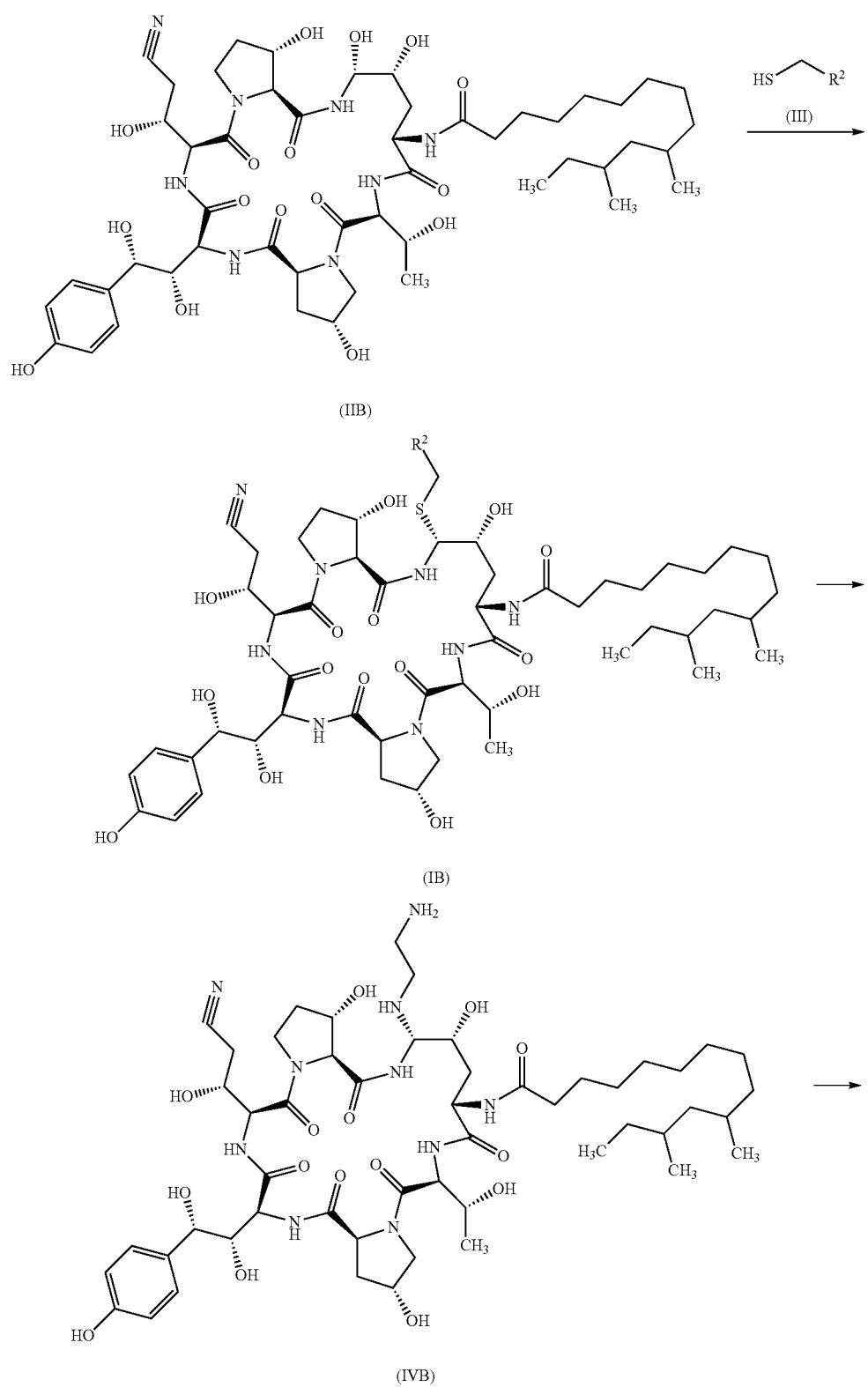

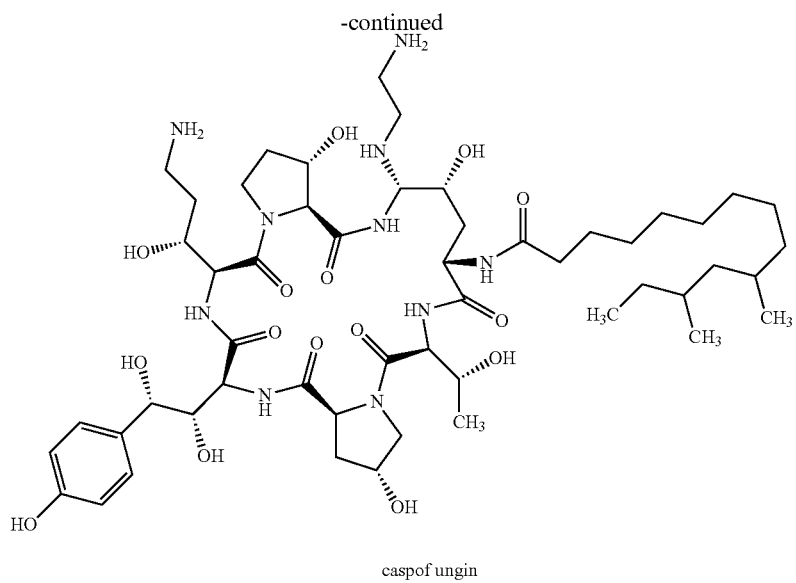

caspofungin

In yet another preferred embodiment of the present invention, said method comprises the following steps:

1) Reaction of intermediate IIC of formula (IIC) with thiol compound III of formula (III) in the presence of organic boronic acid and organic sulfonic acid affords intermediate IC of formula (IC);
2) Reaction of intermediate IC of formula (IC) with ethylenediamine affords intermediate IVC of formula (IVC); and
3) Intermediate of formula (IVC) is reduced to caspofungin.

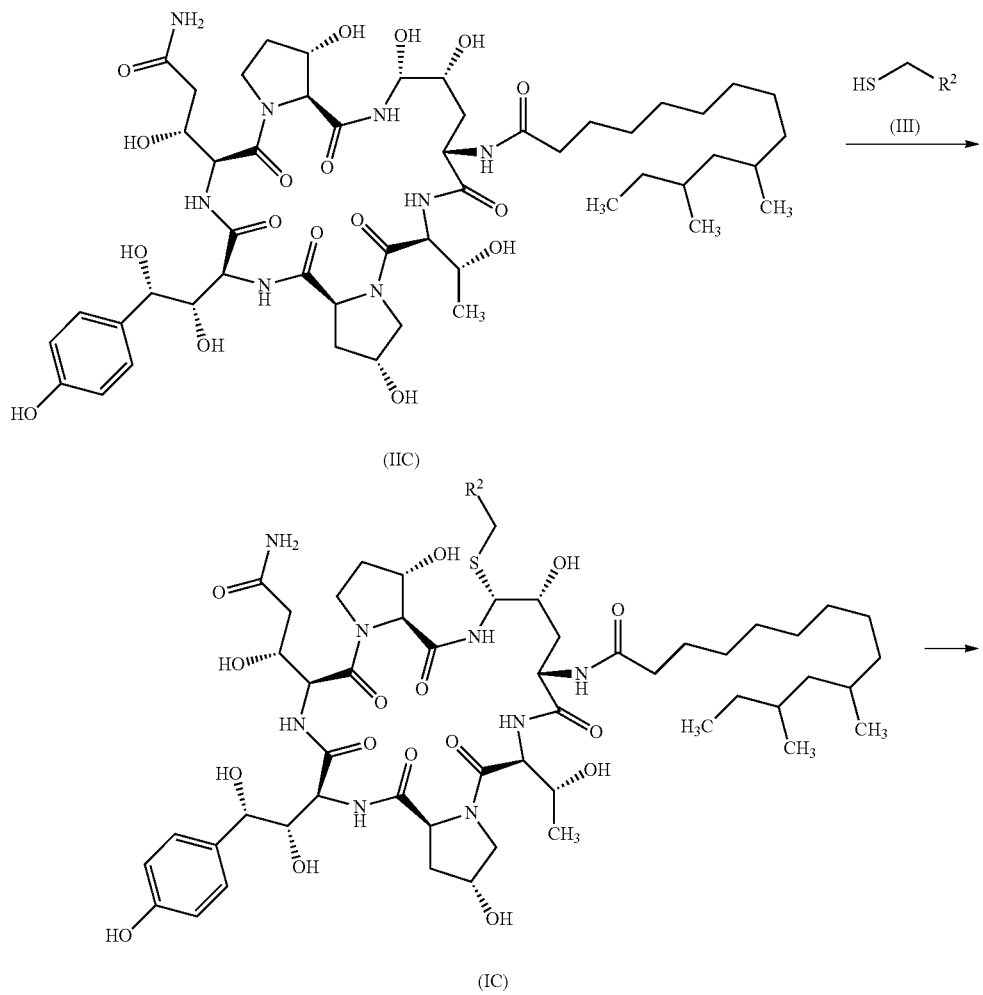

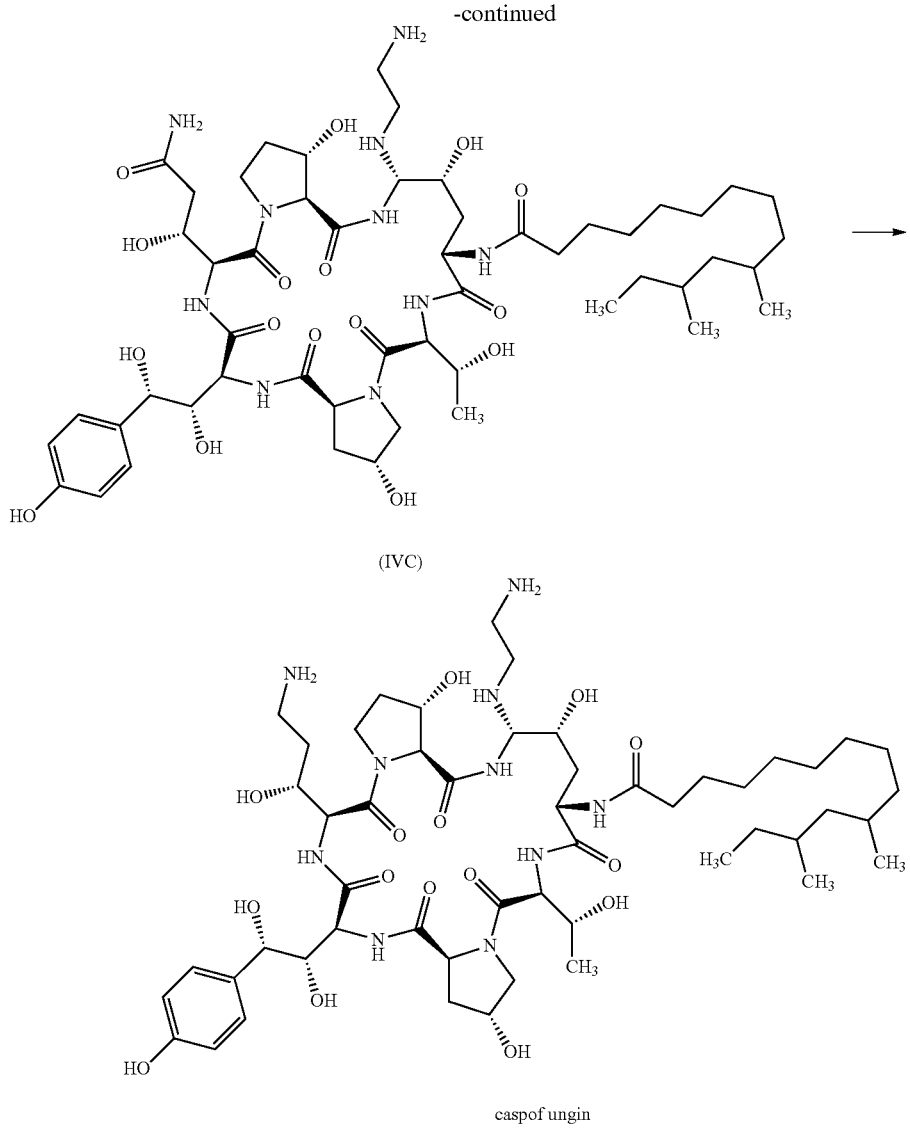

caspofungin

The amino protecting groups in the present invention are known protecting groups suitable for protecting amino groups, referring to protection for the amino group in the literature ("Protective Groups in Organic Synthesis", 5$^{Th}$. Ed. T. W. Greene & P. G. M. Wuts), preferably Boc or Cbz.

The $C_{6-10}$ aromatic groups involved in the present invention can be a single, fused, or poly ring, such as phenyl or naphthyl. The $C_{6-10}$ aromatic group can be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2; R$^6$ and R$^7$ are defined as in formula (I); R$^8$ is linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; and halogen is fluorine, chlorine, bromine or iodine.

Heteroaryl group involved in the present invention refers to five- to ten-membered heteroaromatic systems containing one to four heteroatoms, wherein the heteroatoms may be oxygen, nitrogen or sulfur. Heteoaryl is preferably a five- or six-membered heteroaryl, for example, furyl, thienyl, pyridyl, pyrrolyl, N-alkyl pyrrolyl, pyrimidinyl, pyrazinyl, imidazolyl, tetrazolyl, etc. The heteroaromatic group can be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2; R$^6$ and R$^7$ are defined as in formula (I); R$^8$ is linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; and halogen is fluorine, chlorine, bromine or iodine.

The $C_{1-10}$ alkyl group in the present invention refers to saturated aliphatic hydrocarbon groups, for example, methyl, ethyl, propyl, 2-propyl, n-butyl, isobutyl, tert-butyl or pentyl, etc. A lower alkyl group containing one to four carbon atoms is more preferred, for example, methyl, ethyl, propyl, 2-propyl, n-butyl, isobutyl or tert-butyl. The alkyl group may be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2; R$^6$ and R$^7$ are defined as in formula (I); R$^8$ is linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; and halogen is fluorine, chlorine, bromine or iodine.

The C$_{3-8}$ cycloalkyl group in the present invention refers to a three- to eight-membered carbon monocyclic group which may contain one or more double bonds, but not a fully conjugated π-electron system, for example, cyclopropyl, cyclobutyl, cyclopentyl, cyclopentenyl, cyclohexyl, cyclohexadienyl, cycloheptyl, cycloheptatrienyl, etc. The cycloalkyl group can be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2; R$^6$ and R$^7$ are defined in formula (I); R$^8$ is linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; and halogen is fluorine, chlorine, bromine or iodine.

The C$_{3-10}$ alkenyl group in the present invention can be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2; R$^6$ and R$^7$ are defined as in formula (I); R$^8$ is linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; and halogen is fluorine, chlorine, bromine or iodine.

The C$_{3-10}$ alkynyl group in the present invention can be unsubstituted or substituted, with the substituent groups preferably being one or more groups independently selected from alkyl, alkoxyl, halogen, hydroxyl, nitro, cyano, cycloalkyl, heterocyclic, aryl, heteroaryl, —NR$^6$R$^7$, —C(O)OR$^8$, —OC(O)R$^8$, —O(CH$_2$)$_m$C(O)OR$^8$, —OC(O)NR$^6$R$^7$, carbonyl, —S(O)$_n$R$^8$, —OSO$_2$R$^8$, —SO$_2$NR$^6$R$^7$, or —NHC(O)R$^8$; m is 0, 1 or 2; n is 0, 1 or 2. R$^6$ and R$^7$ are defined as in formula (I); R$^8$ is linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; and halogen is fluorine, chlorine, bromine or iodine.

The organic boronic acid in the present invention is R$^9$B(OH)$_2$, wherein R$^9$ is linear or branched C$_{1-10}$ alkyl, linear or branched C$_{3-10}$ alkenyl or C$_{3-10}$ alkynyl, C$_{3-8}$ cycloalkyl, or unsubstituted or substituted C$_{6-10}$ aryl or heteroaryl, for example, methyl, ethyl, propyl, butyl, phenyl, p-methylphenyl, p-methoxyphenyl, p-chlorophenyl, etc.

The organic sulfonic acid in the present invention is R$^{10}$SO$_3$H, wherein R$^{10}$ is substituted or unsubstituted linear or branched C$_{1-10}$ alkyl, linear or branched C$_{3-10}$ alkenyl or C$_{3-10}$ alkynyl, substituted or unsubstituted C$_{3-8}$ cycloalkyl, or unsubstituted or substituted C$_{6-10}$ aryl or heteroaryl, for example, methyl, trifluoromethyl, phenyl, p-methylphenyl, etc.

DETAILED DESCRIPTION OF THE INVENTION

The present invention will appear clearly for the person skilled in the art upon the following specific examples. These examples only intend to illustrate the invention, while not limiting the scope of the present invention in any way.

The number of the intermediate of formula (I) involved in the examples are shown in following table.

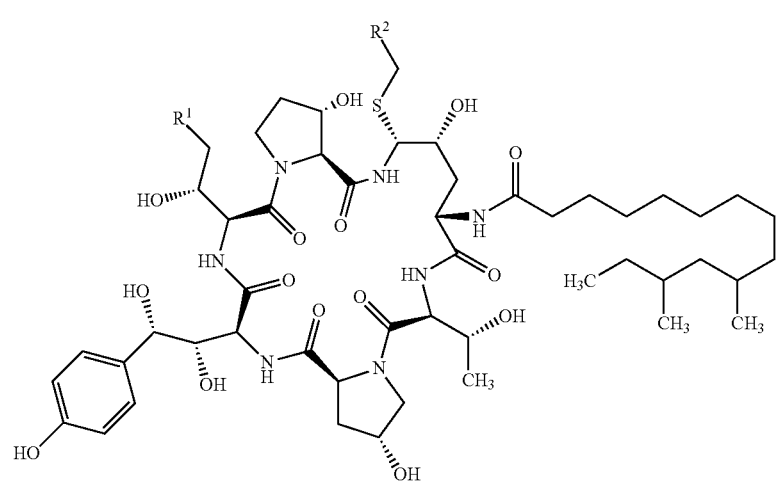

(I)

| Number | R$^1$ | R$^2$ |
|---|---|---|
| IA1 | CH$_2$NH$_2$ | CO$_2$Me |
| IA2 | CH$_2$NH$_2$ | C(=O)NHCH$_2$CH$_2$NH$_2$ |
| IA3 | CH$_2$NH$_2$ | C(=O)NMe$_2$ |
| IA4 | CH$_2$NH$_2$ | CN |
| IB1 | CN | C(=O)NHEt |
| IB2 | CN | C(=O)NMe$_2$ |
| IB3 | CN | CO$_2$Me |
| IB4 | CN | CO$_2$Bu |
| IB5 | CN | CO$_2$H |

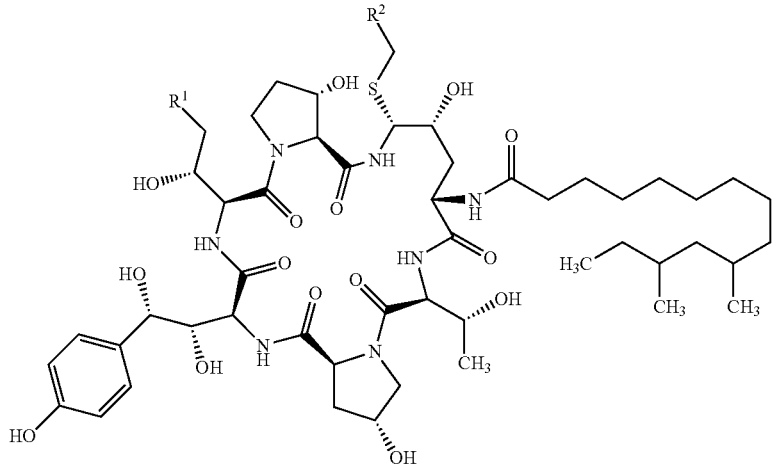
(I)

| Number | R¹ | R² |
|---|---|---|
| IB6 | CN | C(=O)NH$_2$ |
| IB7 | CN | C(=O)NHBu |
| IB8 | CN | ![pyrrolidine carbonyl] |
| IC1 | C(=O)NH$_2$ | CO$_2$Me |
| IC2 | C(=O)NH$_2$ | CO$_2$H |
| IC3 | C(=O)NH$_2$ | CO$_2$Bu |
| IC4 | C(=O)NH$_2$ | CO$_2$$^t$Bu |
| IC5 | C(=O)NH$_2$ | CO$_2$$^c$Pen |
| IC6 | C(=O)NH$_2$ | CO$_2$Ph |
| IC7 | C(=O)NH$_2$ | C(=O)NH$_2$ |
| IC8 | C(=O)NH$_2$ | C(=O)NMe$_2$ |
| IC9 | C(=O)NH$_2$ | C(=O)NHEt |
| IC10 | C(=O)NH$_2$ | C(=O)NHBu |
| IC11 | C(=O)NH$_2$ | ![pyrrolidine carbonyl] |
| IC12 | C(=O)NH$_2$ | C(=O)NH$^c$Pr |
| IC13 | C(=O)NH$_2$ | C(=O)NH$^c$Pen |
| IC14 | C(=O)NH$_2$ | C(=O)NH$^i$Pr |
| IC15 | C(=O)NH$_2$ | C(=O)NHPh |
| IC16 | C(=O)NH$_2$ | Ph |

$^t$Bu = tert-butyl;
$^i$Pr = isopropyl;
$^c$Pr = cyclopropyl
$^c$Pen = cyclopentyl

EXAMPLE 1

Preparation of Compound IA1

A stirred suspension of compound IIA (3.0 g) (which was prepared according to a similar method of U.S. Pat. No. 5,378,804), phenyl boronic acid (0.72 g) and acetonitrile (120 mL) in a three-necked glass flask was mixed with methyl thioglycolate (1.0 g) at −20° C. The resulting mixture was stirred for 30 minutes at this temperature and trifluoromethanesulfonic acid (1.2 g) was added therein dropwise. The reaction mixture was further stirred at −20° C. for 5-6 hours followed by addition of an aqueous solution of sodium acetate. After stirring for another 1-2 hours, the reaction mixture was filtered and the filter cake was washed with aqueous acetonitrile, and dried under vacuum to give white solid product IA1 (2.8 g).

$^1$H NMR (CD$_3$OD, 400 MHz) δ 7.09 (d, 2H), 6.74 (d, 2H), 5.24 (d, 1H), 5.04 (d, 1H), 4.90 (d, 1H) 4.56-4.47 (m), 4.39-4.35 (m, 2H), 4.31-4.25 (m), 4.23-4.21 (m, 3H), 3.99-3.95 (m), 3.80-3.75 (m), 3.63 (s, 3H), 3.04 (t, 2H), 2.42 (dd, 1H), 2.15-1.99 (m, 7H), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1139.61 (M+H$^+$).

EXAMPLE 2

Preparation of Compounds IA2

A stirred suspension of compound IIA (3.0 g), phenyl boronic acid (0.72 g) and acetonitrile (120 mL) in a three-necked glass flask was mixed with N-(2-aminoethyl)mercaptoacetamide (1.26 g) at −20° C. The resulting mixture was stirred for 30 minutes at this temperature and trifluoromethanesulfonic acid (1.2 g) was added therein dropwise. The reaction mixture was further stirred at −20° C. for 5-6 hours followed by addition of an aqueous solution of sodium acetate. After stirring for another 1-2 hours, the reaction mixture was filtered and the filter cake was washed with aqueous acetonitrile, and dried under vacuum to give white solid product IA2 (3.1 g).

MS: 1167.39 (M+H$^+$).

EXAMPLE 3

Preparation of Compound IA3

A stirred suspension of compound IIA (3.0 g), phenyl boronic acid (0.72 g) and acetonitrile (120 mL) in a three-necked glass flask was mixed with N,N-dimethyl-mercaptoacetamide (1.1 g) at −20° C. The resulting mixture was stirred for 30 minutes at this temperature and trifluoromethanesulfonic acid (1.2 g) was added therein dropwise. The reaction mixture was further stirred at −20° C. for 5-6 hours followed by addition of an aqueous solution of sodium acetate. After stirring for another 1-2 hours, the reaction mixture was filtered and the filter cake was washed with aqueous acetonitrile, and dried under vacuum to give white solid product IA3 (3.1 g).

MS: 1152.81 (M+H$^+$).

EXAMPLE 4

Preparation of Compound IA4

A stirred suspension of compound IIA (3.0 g), phenyl boronic acid (0.72 g) and acetonitrile (120 mL) in a three-necked glass flask was mixed with mercaptoacetonitrile (1.5 g) at −20° C. The resulting mixture was stirred for 30 minutes at this temperature and trifluoromethanesulfonic acid (1.2 g) was added therein dropwise. The reaction mixture was further stirred at −20° C. for 5-6 hours followed by addition of an aqueous solution of sodium acetate. After stirring for another 1-2 hours, the reaction mixture was filtered and the filter cake was washed with aqueous acetonitrile, and dried under vacuum to give white solid product IA4 (3.0 g).

$^1$H NMR (CD$_3$OD, 400 MHz) δ 7.15 (d, 2H), 6.79 (d, 2H), 5.34 (d, 1H), 5.04 (d, 1H), 4.64 (m, 3H), 4.53-4.42 (m, 4H), 4.43-4.32 (m, 3H), 4.31-4.25 (m, 5H), 4.23-4.18 (m, 1H), 3.99-3.95 (m, 1H), 3.90-3.8 (m, 3H), 3.73-3.65 (m, 2H), 3.58-3.65 (m, 2H), 3.05-3.18 (m, 2H), 2.40-2.50 (m, 1H), 2.35-2.23 (m, 4H), 2.21-1.98 (m, 6H), 1.97-1.80 (m, 3H), 1.78-1.60 (m, 2H), 1.58-1.41 (m, 2H), 1.40-1.26 (m, 14H), 1.21 (d, 3H), 1.20-1.13 (m, 3H), 0.95-0.85 (m, 10H), 0.68-0.76 (dd, 2H).

MS: 1106.54 (M+H$^+$).

EXAMPLE 5

Preparation of Compound IB1

A suspension of compound IIB (100 mg, prepared according to the similar method of U.S. Pat. No. 5,378,804), phenyl boronic acid (35 mg), and N-ethyl-2-mercaptoacetamide (68 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. The reaction mixture was filtered and the filter cake was washed with acetonitrile/water, collected, and dried under vacuum to give product IB1.

$^1$H NMR (CD$_3$OD, 400 MHz) δ 7.08 (d, 2H), 6.70 (d, 2H), 5.21 (d, 1H), 4.99 (d, 1H), 4.95 (d, 1H), 4.56-4.47 (m, 3H), 4.39-4.21 (m, 6H), 3.99-3.95 (m, 1H), 3.87-3.83 (m, 1H), 3.80-3.75 (m, 2H), 2.95-2.90 (q, 2H), 2.80-2.64 (m, 2H), 2.46 (m, 1H), 2.42 (m, 3H), 2.26-2.12 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (m), 0.81 (m).

MS: 1148. 48 (M+H$^+$).

EXAMPLE 6

Preparation of Compound IB2

A suspension of compound IIB (100 mg), phenyl boronic acid (35 mg), and N,N-dimethyl-2-mercaptoacetamide (68 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB2.

$^1$H NMR (CD$_3$OD, 400 MHz) δ 7.08 (d, 2H), 6.70 (d, 2H), 5.27 (d, 1H), 4.99 (d, 1H), 4.95 (d, 1H), 4.56-4.47 (m, 3H), 4.39-4.21 (m, 6H), 3.99-3.95 (m, 1H), 3.87-3.83 (m, 1H), 3.80-3.75 (m, 2H), 3.04 (s, 3H), 2.89 (s, 3H), 2.80-2.64 (m, 2H), 2.46 (m, 1H), 2.42 (m, 3H), 2.26-2.12 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (m), 0.81 (m).

MS: 1148. 48 (M+H$^+$).

EXAMPLE 7

Preparation of Compound IB3

A suspension of compound IIB (100 mg), phenyl boronic acid (35 mg), and methyl-2-mercaptoacetate (61 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB3.

$^1$H NMR (CD$_3$OD, 400 MHz) δ 7.09 (d, 2H), 6.69 (d, 2H), 5.28 (d, 1H), 4.99 (d, 1H), 4.90 (d, 1H), 4.56-4.47 (m, 3H), 4.39-4.21 (m, 6H), 3.99-3.95 (m, 1H), 3.87-3.83 (m, 1H), 3.80-3.75 (m, 2H), 3.66 (m, 3H), 3.56-3.52 (dd, 1H), 3.49-

3.39 (dd, 1H), 2.80-2.64 (m, 2H), 2.46 (m, 1H), 2.42 (m, 3H), 2.26-2.12 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (m), 0.81 (m).

MS: 1135.38 (M+H$^+$).

EXAMPLE 8

Preparation of Compound IB4

A suspension of compound IIB (100 mg), phenyl boronic acid (35 mg), and butyl-2-mercaptoacetate (85 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB4.

$^1$H NMR (CD$_3$OD, 400 MHz) δ 7.08 (d, 2H), 6.70 (d, 2H), 5.29 (d, 1H), 4.99 (d, 1H), 4.95 (d, 1H), 4.56-4.47 (m, 3H), 4.39-4.21 (m, 6H), 3.99-3.95 (m, 1H), 3.87-3.83 (m, 1H), 3.80-3.75 (m, 2H), 3.58-3.56 (t, 2H), 3.56-3.52 (dd, 1H), 3.49-3.39 (dd, 1H), 2.80-2.64 (m, 2H), 2.46 (m, 1H), 2.42 (m, 3H), 2.26-2.12 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (m), 0.81 (m).

MS: 1178.49 (M+H$^+$).

EXAMPLE 9

Preparation of Compound IB5

A suspension of compound IIB (100 mg), phenyl boronic acid (35 mg), and mercaptoacetic acid (60 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB5.

MS: 1121.16 (M+H$^+$).

EXAMPLE 10

Preparation of Compound IB6

A suspension of compound IIB (100 mg), phenyl boronic acid (35 mg), and mercaptoacetamide (62 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB6.

MS: 1120.44 (M+H$^+$).

EXAMPLE 11

Preparation of Compound IB7

A suspension of compound IIB (100 mg), phenyl boronic acid (35 mg), and N-butyl-2-mercaptoacetamide (86 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB7.

MS: 1176.51 (M+H$^+$).

EXAMPLE 12

Preparation of Compound IB8

A suspension of compound IIB (100 mg), phenyl boronic acid (35 mg), and N-pyrrolyl-2-mercaptoacetamide (86 mg) in anhydrous acetonitrile (8 mL) was added dropwise to a solution of trifluoromethylsulfonic acid (57.3 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was washed with acetonitrile/water, collected, and dried under vacuum to give product IB8.

MS: 1174.58 (M+H$^+$).

EXAMPLE 13

Preparation of Compound IC1

A suspension of compound IIC (PB0, prepared by microbial fermentation) (500 mg), phenyl boronic acid (172 mg), and methyl mercaptoacetate (299 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC1.

$^1$H NMR (CD$_3$OD, 400 MHz) δ 7.09 (d, 2H), 6.70 (d, 2H), 5.29 (d, 1H), 5.1 (d, 1H), 4.99 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.63 (s, 3H), 3.55-3.51 (dd, 1H), 3.36-3.40 (dd, 1H), 2.88 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1153.26 (M+H$^+$).

EXAMPLE 14

Preparation of Compound IC2

A suspension of compound IIC (500 mg), phenyl boronic acid (172 mg), and mercaptoacetic acid (259 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC2.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 2.88 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1139.18 (M+H$^+$)

EXAMPLE 15

Preparation of Compound IC3

A suspension of compound IIC (500 mg), phenyl boronic acid (172 mg), and butyl mercaptoacetate (417 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC3.

MS: 1195.48 (M+H$^+$).

EXAMPLE 16

Preparation of Compound IC4

A suspension of compound IIC (500 mg), phenyl boronic acid (172 mg), and tert-butyl mercaptoacetate (417 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC4.

MS: 1195.48 (M+H$^+$).

EXAMPLE 17

Preparation of Compound IC5

A suspension of compound IIC (500 mg), phenyl boronic acid (172 mg), and cyclopentyl mercaptoacetate (431 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product 105.

MS: 1207.49 (M+H$^+$).

EXAMPLE 18

Preparation of Compound IC6

A suspension of compound IIC (500 mg), phenyl boronic acid (172 mg), and phenyl mercaptoacetate (431 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product 106.

MS: 1215.48 (M+H$^+$).

EXAMPLE 19

Preparation of Compound IC7

A suspension of compound IIC (500 mg), phenyl boronic acid (172 mg), and mercaptoacetamide (259 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC7.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 2.88 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1138.45 (M+H$^+$).

EXAMPLE 20

Preparation of Compound IC8

A suspension of compound IIC (500 mg), phenyl boronic acid (172 mg), and N, N-dimethyl mercaptoacetamide (336 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC8.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.01 (s, 1H), 2.88 (s, 1H), 2.68 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1166.52 (M+H$^+$).

EXAMPLE 21

Preparation of Compound IC9

A suspension of compound IIC (500 mg), phenyl boronic acid (172 mg), and N, N-dimethyl mercaptoacetamide (259 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC9.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 2.88 (dd, 2H), 2.68 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1166.52 (M+H$^+$).

EXAMPLE 22

Preparation of compound IC10

A suspension of compound IIC (500 mg), phenyl boronic acid (172 mg), and N, N-dimethyl mercaptoacetamide (414 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC10.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 2.94-2.91 (t, 2H), 2.68 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 6H), 0.85 (d, 6H).

MS: 1194.53 (M+H$^+$).

EXAMPLE 23

Preparation of Compound IC11

A suspension of compound IIC (500 mg), phenyl boronic acid (172 mg), and N-pyrrolyl mercaptoacetamide (410 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC11.

$^1$H-NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.18-3.14 (m, 4H), 2.68 (dd, 1H), 2.46 (dd, 1H), 2.42 (dd, 1H), 2.26-2.18 (m), 2.10-2.03 (m), 1.94-1.90 (m, 4H), 1.87-1.85 (m), 1.63-1.52 (m), 1.51-1.46 (m), 1.45-1.39 (m), 1.38-1.20 (m), 1.14 (d), 1.12-1.03 (m), 0.91 (dt, 2H), 0.87 (d, 3H), 0.85 (d, 6H);

MS: 1192.56 (M+H$^+$).

EXAMPLE 24

Preparation of Compound IC12

A suspension of compound IIC (500 mg), phenyl boronic acid (172 mg), and N-cyclopropyl mercaptoacetamide (370 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC12.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.21-3.09 (dd, 1H), 2.68 (dd, 1H), 2.46 (dd, 1H), 2.42 (dd, 1H), 2.26-2.18 (m), 2.10-2.03 (m), 1.87-1.85 (m), 1.63-1.52 (m), 1.51-1.46 (m), 1.45-1.39 (m), 1.38-1.20 (m), 1.14 (d), 1.12-1.03 (m), 0.91 (dt, 2H), 0.87 (d, 3H), 0.85 (d, 6H) 0.68~0.50 (m, 4H);

MS: 1178.46 (M+H$^+$).

EXAMPLE 25

Preparation of Compound IC13

A suspension of compound IIC (500 mg), phenyl boronic acid (172 mg), and N-cyclopentyl mercaptoacetamide (450 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC13.

$^1$H NMR (CD$_3$OD, 400 MHz) δ 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.21-3.09 (dd, 1H), 2.68 (dd, 1H), 2.46 (dd, 1H), 2.42 (dd, 1H), 2.26-2.18 (m), 2.10-2.03 (m), 1.94-1.90 (m, 4H), 1.87-1.85 (m), 1.63-1.52 (m), 1.51-1.46 (m), 1.45-1.39 (m), 1.38-1.20 (m), 1.14 (d), 1.12-1.03 (m), 0.91 (dt, 2H), 0.89-0.85 (m, 15H);

MS: 1206.50 (M+H$^+$).

EXAMPLE 26

Preparation of Compound IC14

A suspension of compound IIC (500 mg), phenyl boronic acid (172 mg), and N-isopropyl mercaptoacetamide (370 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC14.

MS: 1180.50 (M+H$^+$).

EXAMPLE 27

Preparation of Compound IC15

A suspension of compound IIC (500 mg), phenyl boronic acid (172 mg), and N-phenyl mercaptoacetamide (370 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC15.

MS: 1214.65 (M+H$^+$).

EXAMPLE 28

Preparation of Compound IC16

A suspension of compound IIC (500 mg), phenyl boronic acid (172 mg), and benzyl mercaptan (350 mg) in anhydrous acetonitrile (30 mL) was added dropwise to a solution of trifluoromethylsulfonic acid (282 mg) in acetonitrile at −15° C. under nitrogen atmosphere. The reaction mixture was stirred at the same temperature for 4-6 hours to complete the reaction. After addition of sodium acetate aqueous solution and stirring for 1-2 hours, water (90 mL) was added to the reaction mixture followed by stirring for another one hour. Then the reaction mixture was filtered and the filter cake was collected and dried under vacuum to give product IC16.

$^1$H NMR (CD$_3$OD, 400 MHz) δ 7.30-7.27 (d, 2H), 7.24-7.2 (t, 3H), 7.17-7.15 (d, 1H), 7.09 (d, 2H), 6.70 (d, 2H), 5.24 (d, 1H), 5.04 (d, 1H), 4.90 (d, 1H), 4.56-4.47 (m), 4.39-4.35 (m, 2H), 4.31-4.25 (m), 4.23-4.21 (m, 3H), 3.99-3.95 (m), 3.80-3.75 (m), 3.63 (s, 3H), 3.55-3.51 (dd, 1H), 3.36-3.40 (dd, 1H), 2.88 (dd, 1H), 2.46 (dd, 1H), 2.42 (dd, 1H), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d), 1.12-1.03 (m), 0.91 (dt, 1H), 0.87 (d, 3H), 0.85 (d, 6H).

MS: 1171.10 (M+H$^+$).

EXAMPLE 29

Preparation of Caspofungin

Compound IA1 (70 mg) was dissolved in methanol (0.5 mL) at 15° C. Ethylenediamine (0.7 mL) was added to the solution at 5° C. and the resulting mixture was stirred at 40° C. for 20 hours. After evaporation of methanol, acetonitrile was added to the residue and the resulting mixture was stirred, and filtered under nitrogen atmosphere to give crude product as a solid which was dried under vacuum. Purification via a C-18 silica gel column gave final product caspofungin.

MS: 1093.21 (M+H$^+$).

EXAMPLE 30

Preparation of Caspofungin

Step 1):
A stirring solution of compound IB1 (800 mg) in methanol (20 mL) in a three-necked glass flask was mixed with ethylenediamine (20 mL) at 30° C. and the resulting reaction mixture was stirred for 18 hours at this temperature. After concentration of the reaction solution, acetonitrile (40 mL) was added to the residue and the resulting mixture was stirred for 20-30 minutes and filtered. The filter cake was collected and dried to give product IVB.

MS: 1089.22 (M+H$^+$).

Step 2):
A solution of compound IVB (100 mg) in ethanol (9 mL) and water (1 mL) was mixed with acetic acid (1 mL) and Pd/C (10%, 50 mg). The resulting reaction mixture was stirred for 10 hours under 3 atm of hydrogen pressure at 20° C. After filtration to remove the catalyst and evaporation to remove the solvent, the residue was dissolved in water (20 mL) and extracted with ethyl acetate (10 mL×2). The aqueous phase was collected and lyophilized to give crude caspofungin which was further purified via a C-18 silica gel column to give the final product caspofungin.

MS: 1093.21 (M+H$^+$).

EXAMPLE 31

Preparation of Caspofungin

Step 1):
A stirring solution of compound IC1 (800 mg) in methanol (20 mL) in a three-necked glass flask was mixed with ethylenediamine (20 mL) at 30° C. and the resulting reaction mixture was stirred for 18 hours at this temperature. After concentration of the reaction solution, acetonitrile (40 mL) was added to the residue and the resulting mixture was stirred for 20-30 minutes and filtered. The filter cake was collected and dried to give product IVC.

MS: 1107.29 (M+H$^+$).

Step 2):
A solution of compound IVC (100 mg) in anhydrous tetrahydrofuran (THF) (20 mL) in a three-necked glass flask was added with phenylboronic acid (33 mg) under nitrogen atmosphere and the resulting reaction mixture was stirred overnight and then cooled to 10° C. The reaction mixture was mixed with bis(trimethylsilyl)trifluoroacetamide (140 mg) and stirred for 3 hours. Then the reaction mixture was brought to −15° C. and mixed with borane in THF solution (1.0 M, 1.35 mL). The resulting mixture was stirred for 6 hours at −15° C. The reaction was quenched by addition of 2 N hydrochloric acid (2 mL) and then mixed with water (20 mL). The aqueous phase was separated and extracted with ethyl acetate (10 mL×2). The aqueous phase was collected and lyophilized to give crude caspofungin which was further purified via a C-18 silica gel column to give the final product caspofungin.

MS: 1093.21 (M+H$^+$).

Due to the detailed description of the particular embodiments of the present invention, some modifications and variants are obvious for the person skilled in the art and will be contained in the scope of the present invention.

What is claimed is:

1. An intermediate of formula (I) for the synthesis of caspofungin:

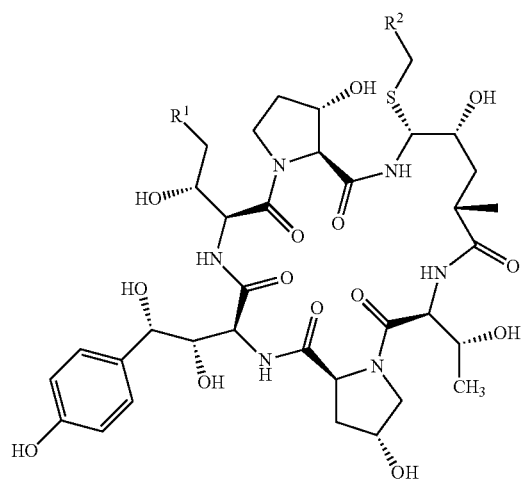

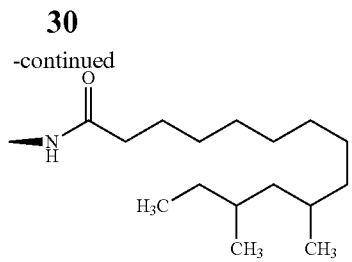

wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or an amino protecting group; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle; and $R^6$ and $R^7$ are not an amino or methoxy group at the same time.

2. The intermediate according to claim 1, wherein $R^1$ is $C(=O)NH_2$, CN or $CH_2NH_2$; $R^2$ is CN, $CO_2H$, $CO_2Me$, $CO_2Et$, $CO_2Bu$, $CO_2{}^tBu$, $CO_2Ph$, $C(=O)NH_2$, $C(=O)NMe_2$, $C(=O)NHEt$, $C(=O)NHBu$, $C(=O)NHCH_2CH_2NH_2$, $C(=O)NH^cPr$, $C(=O)NH^iPr$, $C(=O)NH^cPen$, $C(=O)NHBu$, $C(=O)NHPh$ or phenyl.

3. A method of preparing an intermediate of formula (I):

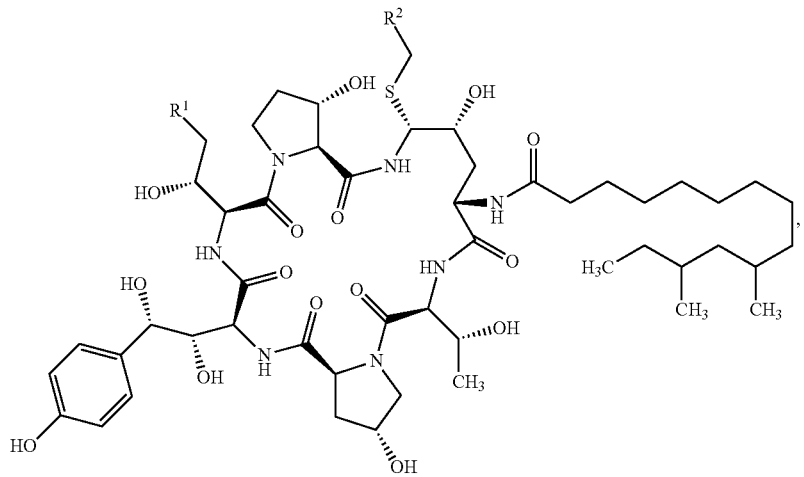

comprising reacting an intermediate of formula (II) with a thiol compound of formula (III) to give the intermediate of formula (I):

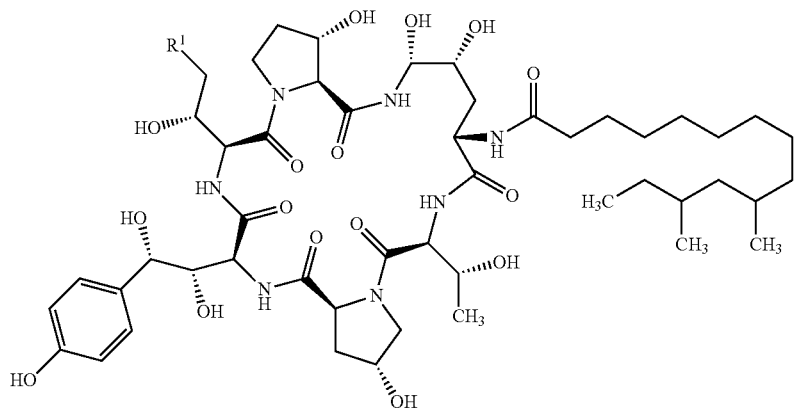

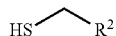

(III)

wherein, $R^1$ is C(=O)NH$_2$, CN, or CH$_2$NR$^3$R$^4$; $R^2$ is CN, CO$_2$R$^5$, C(=O)NR$^6$R$^7$ or substituted or unsubstituted C$_{6-10}$ aryl or heteroaryl; $R^3$ and $R^4$ are each independently hydrogen or an amino protecting group; $R^5$ is hydrogen, linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; $R^6$ and $R^7$ are each independently hydrogen, amino, methoxy, linear or branched C$_{1-10}$ alkyl, linear or branched C$_{3-10}$ alkenyl or C$_{3-10}$ alkynyl, C$_{3-8}$ cycloalkyl, or substituted or unsubstituted C$_{6-10}$ aryl or heteroaryl; or $R^6$ and $R^7$ together with a nitrogen atom form a five- to eight-membered heterocycle; and $R^6$ and $R^7$ are not an amino or methoxy group at the same time.

4. The method according to claim 3, wherein the reaction proceeds in the presence of organic boronic acid and organic sulfonic acid.

5. The method according to claim 4, wherein the organic boronic acid is phenyl boronic acid and the organic sulfonic acid is trifluoromethanesulfonic acid.

6. A method of preparing caspofungin, comprising a step of reacting the intermediate of formula (I) according to claim 1 with ethylenediamine, wherein when $R^1$ in the intermediate of formula (I) is not CH$_2$NH$_2$, $R^1$ is reduced to CH$_2$NH$_2$ or undergoes amino-deprotection before or after the reaction with ethylenediamine, (I)

[structure of formula (I)]

7. The method according to claim 6, wherein $R^1$ is reduced to CH$_2$NH$_2$ or undergoes amino-deprotection after the reaction with ethylenediamine.

8. The method according to claim 6, wherein the method comprises a step of reacting an intermediate of formula (II) with a thiol compound of formula (III) to give the intermediate of formula (I);

(II)

[structure of formula (II)]

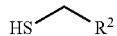

(III)

wherein, $R^1$ is $C(=O)NH_2$, CN, or $CH_2NR^3R^4$; $R^2$ is CN, $CO_2R^5$, $C(=O)NR^6R^7$ or substituted or unsubstituted $C_{6-10}$ aryl or heteroaryl; $R^3$ and $R^4$ are each independently hydrogen or an amino protecting group; $R^5$ is hydrogen, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; $R^6$ and $R^7$ are each independently hydrogen, amino, methoxy, linear or branched $C_{1-10}$ alkyl, linear or branched $C_{3-10}$ alkenyl or $C_{3-10}$ alkynyl, $C_{3-8}$ cycloalkyl, or substituted or unsubstituted $C_{6-10}$ aryl or heteroaryl; or $R^6$ and $R^7$ together with a nitrogen atom form a five- to eight-membered heterocycle; and $R^6$ and $R^7$ are not an amino or methoxy group at the same time.

9. The method according to claim 8, wherein the reaction between the intermediate of formula (II) and the thiol compound of formula (III) proceeds in the presence of organic boronic acid and organic sulfonic acid.

10. The method according to claim 9, wherein the organic boronic acid is phenyl boronic acid and the organic sulfonic acid is trifluoromethanesulfonic acid.

11. The method according to claim 6, wherein $R^1$ is CN.

12. The method according to claim 6, wherein $R^1$ is $C(=O)NH_2$.

13. The method according to claim 6, wherein $R^1$ is $CH_2NR^3R^4$, and $R^3$ and $R^4$ are each independently hydrogen or an amine protecting group.

14. The intermediate of claim 1, wherein $R^3$ and $R^4$ are each independently Boc or Cbz.

15. The intermediate of claim 1, wherein $R^6$ and $R^7$ together with a nitrogen atom form a five- or six-membered heterocycle.

16. The intermediate of claim 2, wherein $R^2$ is $CO_2H$, $CO_2Me$, or $C(=O)NHCH_2CH_2NH_2$.

17. The method of claim 3, wherein $R^3$ and $R^4$ are each independently Boc or Cbz.

18. The method of claim 3, wherein $R^6$ and $R^7$ together with a nitrogen atom form a five- or six-membered heterocycle.

19. The method of claim 6, wherein $R^3$ and $R^4$ are each independently Boc or Cbz.

20. The method of claim 6, wherein $R^6$ and $R^7$ together with a nitrogen atom form a five- or six-membered heterocycle.

21. The intermediate according to claim 1, wherein $R^2$ is CN, $CO_2R^5$, or $C(=O)NR^6R^7$.

* * * * *